United States Patent [19]

Winner

[11] Patent Number: Plant 6,066

[45] Date of Patent: Dec. 22, 1987

[54] VARIETY OF GERANIUM NAMED DIPLOMAT

[75] Inventor: Blair L. Winner, Lompoc, Calif.

[73] Assignee: Denholm Seeds, Lompoc, Calif.

[21] Appl. No.: 802,981

[22] Filed: Nov. 29, 1985

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Webb, Burden, Robinson & Webb

[57] ABSTRACT

A new geranium cultivar is distinguished by its compact, upright, well branched plant of excellent conformation. The new cultivar has attractive foliage with moderate sized leaves with seasonal, attractive dark zones. The numerous, long lasting, nonshattering flowers, well placed relative to the foliage, are a brilliant dark red in color.

1 Drawing Figure

BACKGROUND OF THE NEW PLANT

The present invention comprises a new and distinct cultivar of *Pelargonium hortorum* which is a zonal geranium known by the varietal name Diplomat. The new variety (Oglevee No. 882, Denholm No. 41996-3) was discovered in a selective breeding program by Mr. Blair L. Winner and is a selection from the selfing of a selection from the crossing of "Glacier Crimson" (U.S. Plant Pat. No. 5,057, formerly "Bruni") and the unpatented variety "Phyliss".

The new cultivar was discovered in August of 1982 at Denholm Seeds in Lompoc, Calif., was first asexually reproduced by cuttings by Denholm Seeds at Lompoc, Calif., and has been repeatedly asexually reproduced by cuttings at Oglevee Associates, Inc. in Connellsville, Pa. over a 36 month period. It has also been trial and field tested at Connellsville, Pa. during the summers of 1983, 1984 and 1985. It has been found to retain its distinctive characteristics through successive propagations.

The new cultivar is most similar to "Glacier Crimson" but has a more vigorous growing habit, greater heat tolerance, more floriferous and is not as dwarfed as "Glacier Crimson".

The new cultivar, when grown in a glass greenhouse in Connellsville, Pa. using full natural light, 60° F. night temperature, 68° F. day temperature and 71° F. vent temperature and grown in a soilless media of constant fertilizer of 275–300 parts per million nitrogen and potassium, has a response time from a rooted cutting to a flowering plant in a 10 cm pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the cultivar. The data which define these characteristics were collected from asexual reproductions carried out by Oglevee Associates, Inc. in Connellsville, Pa. The plant histories were taken on plants blossomed under natural light in a greenhouse and color readings were taken indoors under 200 foot candles of cool, white fluorescent light. Color references are primarily to the R.H.S. Colour Chart of The Royal Horticultural Society of London.

THE PLANT

Classification:
- *Botanical.*—*Pelargonium hortorum.*
- *Commercial.*—Zonal geranium.

Form: Bush; compact; semi-dwarf; free basal branching; blooms close to foliage.
Height: 16–24 cm from media surface.
Growth: Free branching from base; short internodes.
Strength: Stands upright without artificial support.
Foliage: Stalked leaf attachment; zoning.
Leaves:
- *Size.*—4.5–9.0 cm across.
- *Shape.*—Reniform; cordate base.
- *Margin.*—Crenate.
- *Texture.*—Pubescent.
- *Color.*—Top: Margin and center green group 138B; zone-green group 137C. Bottom: Yellow-green group 146C. Zonation: Seasonal dark green/-bronze.
- *Ribs and veins.*—Palmate.

Petioles: Green group 143C; 2.5–5.5 cm in length.
Stem:
- *Color.*—Green group 143C.
- *Internodes.*—1–2 cm in length.

INFLORESCENCE

Blooming habit: Continuous; upright; semi-double; hemispherical in shape.
Size: 8–10 cm across.
Borne: Umbel; florets on pedicel; pedicels on peduncle.
Florets:
- *Form.*—Round; slightly flat to cupped; regular.
- *Color.*—Top: Red group 44B. Bottom: Red group 41C.
- *Petals.*—10–14 in number separate — not united; margin entire, palmate venation; obovate.
- *Size.*—1.5–2.5 cm across.
- *Texture and appearance.*—Smooth; reflective flecks.

Petaloids:
- *Quantity.*—3–5.
- *Color.*—Front: Red group 44B. Back: Red group 41C.

Pedicel:

*Length.*—2–3 cm.

*Elliptic to linear.*—Some lobed.

Peduncle: Arise from node opposite leaf node; 6–10 cm in length; yellow-green group 144B.

Persistence: Nonshattering, persistent, florets.

Disease resistance: Good resistance to Botrytis and Alternaria leaf spots.

REPRODUCTIVE ORGANS

Stamens, anthers: Light pink when young, orange to orange brown when mature.

Filaments: White at base; reddish coloring toward tip; irregular in shape; some petaloid; flat at base and twisted at tip; 6–8 mm in length.

Pollen: Golden yellow-color initially.

Pistils:

*Number.*—1 with 5 parted stigma.

*Length.*—8 mm.

Stigma: 5 parted; color same as petal.

Style: 1; 2 mm in length; same color as petals.

Ovaries: 5 mm in length; yellow-green; very pubescent (0.1–0.5 mm).

Fruit: None observed.

The new cultivar is a compact, upright, well branched plant of excellent conformation. It has attractive foliage with moderate sized leaves with seasonal, attractive dark zones. The numerous, long lasting, nonshattering flowers are well placed relative to the foliage and are a unique, brilliant dark red in color.

The new cultivar has been fingerprinted by Dr. Richard Craig and his associates at Penn State University in State College, Pa. The fingerprinting was conducted on a Waters High Performance Liquid Chromatograph equipped with an automatic injection system, dual pumps, solvent programmer, data module, variable wavelength detector, and a $C_{18}$ column. The anthocyanin and flavonol chemical markers utilizing flower petals as an adjunct for cultivar identification were determined.

The anthocyanin and flavonol concentrations of petals just after anthesis of the cultivar Diplomat florets sampled in April of 1985 are compared with the cultivar "Bruni" (U.S. Plant Pat. No. 5,057) and presented below in Tables 1 and 2. Results are based on the average of multiple tests. It should be noted that changes in environment can influence the biosynthesis.

TABLE 1

| | Anthocyanin Concentration ug anthocyanin 3,5 diglucoside/g fresh wt. | | | | | |
|---|---|---|---|---|---|---|
| Cultivar | Delphinidin | Cyanidin | Pelargonidin | Peonidin | Malvidin | Total |
| DIPLOMAT | 27 | 150 | 2874 | 1376 | 618 | 5045 |
| XCR - Bruni | — | 78 | 5251 | 2418 | — | 7747 |

TABLE 2

| | Flavonol Concentration ug/g fresh wt. | | | | |
|---|---|---|---|---|---|
| Cultivar | Qu3-[z] rhagal | Qu3-rut | Qu3-gal | Qu3-glu | Km3-rhagal |
| DIPLOMAT | t | t | t | 21 | 59 |
| XCR - Bruni | 11 | 34 | — | t | 307 |

| Cultivar | Km3-gal | Km3-rut | Km3-xyl | Km3-arab | Km3-rha | Total |
|---|---|---|---|---|---|---|
| DIPLOMAT | 119 | 180 | t | 32 | ND[x] | 431 |
| XCR - Bruni | 47 | 1257 | 13 | 49 | 185 | 1908 |

[z]Abbreviations: Km = Kaempferol; Qu = Quercetin; arab = arabinoside; gal = galactoside; glu = glucoside; rha = rhamnoside; rhagal = rhamnosylgalactoside; rut = rutinoside; xyl = xyloside. t = trace <10 ug. ND[x] = not determined

I claim:

1. A new and distinct variety of geranium plant substantially as herein shown and described and parts therefor.

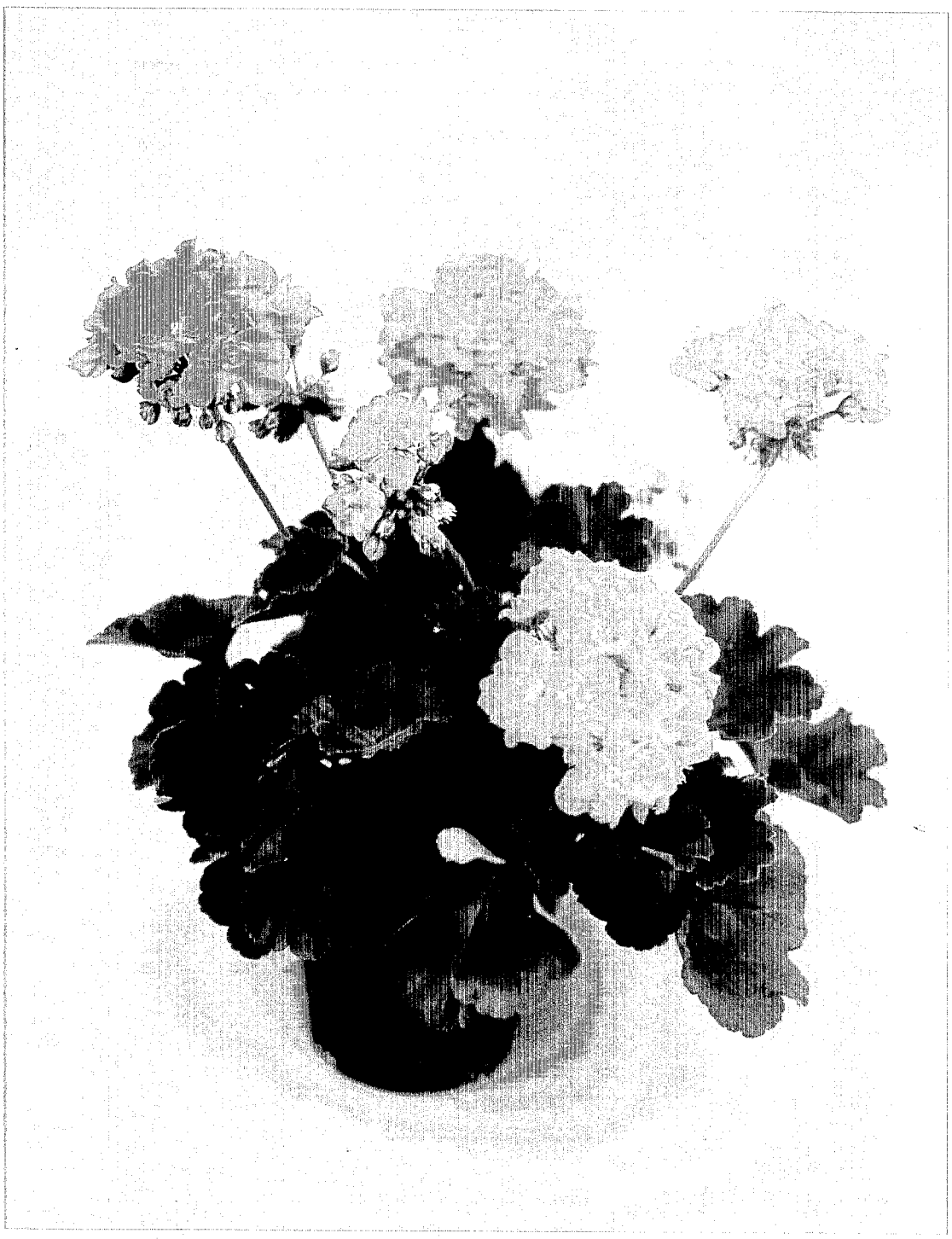

* * * * *